United States Patent [19] [11] 4,187,316
Metcalf et al. [45] Feb. 5, 1980

[54] SUBSTITUTED 1,5-CYCLOHEXADIENE CARBOXYLIC ACID DERIVATIVES

[75] Inventors: Brian W. Metcalf, Strasbourg; Michel Jung, Illkirch, both of France

[73] Assignee: Merrell Toraude et Compagnie, Strasbourg, France

[21] Appl. No.: 868,860

[22] Filed: Jan. 12, 1978

[51] Int. Cl.² ............... A61K 31/215; C07C 61/22
[52] U.S. Cl. .............. 424/305; 260/501.11; 424/309; 424/316; 424/319; 424/300; 424/320; 424/324; 560/47; 560/48; 560/115; 560/125; 562/456; 562/457; 562/510
[58] Field of Search ............... 260/514 J, 501.11; 424/316, 305, 319; 560/125; 562/510

[56] References Cited
U.S. PATENT DOCUMENTS

| 3,959,356 | 5/1976 | Metcalf | 560/172 |
|---|---|---|---|
| 3,960,927 | 6/1976 | Metcalf | 560/38 |

OTHER PUBLICATIONS
Rando and Bangerter, J.A.C.S., 98, 6762 (1976).

Primary Examiner—James O. Thomas, Jr.
Assistant Examiner—G. T. Breitenstein
Attorney, Agent, or Firm—L. Ruth Hattan; Eugene O. Retter; George W. Rauchfuss, Jr.

[57] ABSTRACT

Compounds of the following general formula and salts thereof are irreversible inhibitors of γ-aminobutyric acid transaminase:

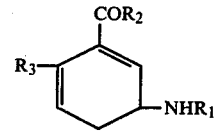

wherein $R_1$ is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched, the radical

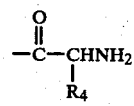

wherein $R_4$ is hydrogen, a straight or branched alkyl group having from 1 to 4 carbon atoms, benzyl or p-hydroxybenzyl; $R_2$ is hydroxy, a straight or branched alkoxy group of from 1 to 8 carbon atoms, the group

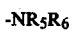

-$NR_5R_6$ wherein each of $R_5$ and $R_6$ is hydrogen or a straight or branched alkyl group having from 1 to 4 carbon atoms, or

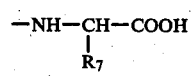

wherein $R_7$ is hydrogen, a straight or branched lower alkyl group of from 1 to 4 carbon atoms, benzyl or p-hydroxybenzyl; and $R_3$ is hydrogen or bromine.

9 Claims, No Drawings

SUBSTITUTED 1,5-CYCLOHEXADIENE CARBOXYLIC ACID DERIVATIVES

FIELD OF INVENTION

This invention relates to novel 3-amino substituted 1,5-cyclohexadiene carboxylic acid and derivatives which possess useful pharmacological properties.

BACKGROUND OF INVENTION

Several previous studies have shown that γ-aminobutyric acid is a major inhibitory transmitter of the central nervous system as reported, for example, by S. Kranjevic, Physiological Reviews 54, 418–540 (1974) and that disturbance of the excitation and inhibition interplay can lead to diseased states such as Huntington's chorea (The Lancet, Nov. 9, 1974, pp. 1122–1123), Parkinsonism, schizophrenia, epilepsy, depression, hyperkinesis and manic depression disorders, E. Roberts, Biochem. Pharmacol. 23, 2637–2649 (1974). Certain compounds are known to elevate brain levels of γ-aminobutyric acid, for example, n-dipropylacetate (Simler et al., Biochem. Pharm., 22 1701 (1973)) by competitively inhibiting γ-aminobutyric acid transaminase resulting in a reversible effect which lasts for only about 2 hours. Also, 4-aminotetrolic acid (P. M. Beart et al., J. Neurochem. 19 1849 (1972)) is known to be a competitive reversible inhibitor of γ-aminobutyric acid transaminase.

U.S. Pat. Nos. 3,959,356 and 3,960,927 cover respectively acetylenic and olefinic derivatives of amino acids which are irreversible inhibitors of γ-aminobutyric acid transaminase.

The natural product gabaculine or 5-amino-1,3-cyclohexadiene-1-carboxylic acid is known to be a selective irreversible inhibitor of γ-aminobutyric acid transaminase in vitro and in vivo (Kobayashi et al., Tetrahedron letters 1976, 537; R. Rando and F. W. Bangerter, Biochem. Biophys. Res. Comm. 76, 1276 (1977); and J. Am. Chem. Soc. 98, 6762, (1976); Kobayashi et al., FEBS. Lett. 76, 207, (1977); and R. D. Allan et al., Neuroscience Lett. 4, 51 (1977)), gabaculine acting as a substrate for the transaminase. Gabaculine thus avoids the depletion of 4-aminobutyric acid which depletion is connected with central nervous system diseases like Parkinsonism and epilepsy.

It has now been found that compounds of the present invention are irreversible inhibitors of γ-amino butyric acid transaminase of a better efficiency than gabaculine and certain other known irreversible inhibitors of γ-aminobutyric acid transaminase rendering said compounds particularly useful in the treatment of aforesaid diseased states.

SUMMARY OF THE INVENTION

The compounds of the present invention are represented by the following general Formula I:

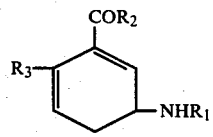

Formula I wherein $R_1$ is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched, or the radical

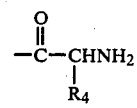

wherein $R_4$ is hydrogen, a straight or branched alkyl group of from 1 to 4 carbon atoms, benzyl or p-hydroxybenzyl; $R_2$ is hydroxy, a straight or branched alkoxy group of from 1 to 8 carbon atoms, $-NR_5R_6$ wherein each of $R_5$ and $R_6$ is hydrogen or a straight or branched alkyl group of from 1 to 4 carbon atoms or the radical

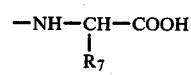

wherein $R_7$ is hydrogen, a straight or branched alkyl group of from 1 to 4 carbon atoms, benzyl or p-hydroxybenzyl; and $R_3$ is hydrogen or bromine. The pharmaceutically acceptable salts of the compounds of general Formula I are also included within the scope of the present invention.

Illustrative examples of straight chain lower alkyl groups of from 1 to 4 carbon atoms referred to herein are methyl, ethyl, n-propyl and n-butyl, and of branched lower chain alkyl groups of from 1 to 4 carbon atoms are isopropyl, isobutyl, and tert-butyl.

Illustrative examples of straight chain lower alkoxy groups of from 1 to 4 carbon atoms as used herein are methoxy, ethoxy, n-propoxy and n-butoxy, and of branched chain lower alkoxy groups of from 1 to 4 carbon atoms are isopropoxy, isobutoxy, and tert-butoxy.

Illustrative examples of straight or branched alkoxy groups of from 1 to 8 carbon atoms as used herein are methoxy, ethoxy, n-propoxy, isopropoxy, n-butoxy, tert-butoxy, neopentoxy, pentoxy, octyloxy, heptyloxy and hexyloxy.

Illustrative examples of pharmaceutically acceptable salts of the compounds of this invention include non-toxic acid addition salts formed with inorganic acids, such as, hydrochloric, hydrobromic, sulfuric and phosphoric acid, and organic acids such as trifluoroacetic, methane sulfonic, salicylic, maleic, malonic, tartaric, citric and ascorbic acids and non-toxic salts formed with inorganic and organic bases, such as, those of alkali metals, for example, sodium, potassium and lithium, alkaline earth metals, for example, calcium and magnesium, light metals of Group III A, for example, aluminum, organic amines, such as, primary, secondary or tertiary amines, for example, cyclohexylamine, ethylamine, pyridine, methylaminoethanol, ethanolamine, and piperidine. The salts of the compounds of the present invention are prepared by conventional means.

Illustrative examples of compounds of this invention are the following:

3-amino-1,5-cyclohexadiene carboxylic acid,
methyl or ethyl 3-amino-1,5-cyclohexadiene carboxylate,
N-methyl-3-amino-1,5-cyclohexadiene carboxamide, N-ethyl-3-amino-1,5-cyclohexadiene carboxamide,
N-propyl-3-amino-1,5-cyclohexadiene carboxamide,
N,N-di-n-butyl-3-amino-1,5-cyclohexadiene carboxamide,
methyl 3-(tert-butoxycarbonylamino)-1,5-cyclohexadiene carboxylate,
3-amino-1,5-cyclohexadiene carboxamide,
N-(3-amino-1,5-cyclohexadienyl)carbonylalanine,
3-acetamido-1,5-cyclohexadiene carboxylic acid,
3-alanylamino-1,5-cyclohexadiene carboxylic acid,
3-amino-6-bromo-1,5-cyclohexadiene carboxylic acid, and
methyl 3-tert-butoxycarbonylamino-6-bromo-1,5-cyclohexadiene carboxylate.

Preferred compounds of this invention are those wherein $R_1$ is hydrogen. Another preferred embodiment of this invention are compounds wherein $R_2$ is hydroxy. The most preferred embodiment of this invention are compounds wherein $R_1$ is hydrogen, $R_2$ is hydroxy and $R_3$ is hydrogen or bromine with compounds wherein $R_3$ is hydrogen being more preferred.

The compounds of the present invention have a variety of pharmacological utilities. The compounds of this invention are useful as sedatives. The compounds of general Formula I and pharmaceutically acceptable salts thereof are useful as inhibitors of γ-aminobutyric acid transaminase resulting in an increase in brain levels of γ-aminobutyric acid rendering said compounds useful in the treatment of disorders of the central nervous system functions consisting of involuntary movements such as associated with Huntington's chorea, Parkinsonism, extra-pyramidal effects of drugs, for example, neuroleptics, seizure disorders associated with epilepsy, alcohol withdrawal and barbiturate withdrawal, psychosis associated with schizophrenia, depression and manic depression and hyperkinesis. Compounds of this invention are also useful as hypothermic agents, myorelaxants, cholinergic agents, antibacterial agents, anticonvulsants, analgesics, anorexigenic agents, antiobesity agents, tranquilizers, sedatives and central nervous system stimulants.

The sedative properties of the compounds of the present invention may be determined by measuring spontaneous motor activity in rodents by the procedures described by P. Dews, Brit. J. Pharmacol. 8, 46 (1953). For example, administration of between 25 to 100 mg/kg (miligrams per kilogram) of the compound 3-amino-1,5-cyclohexadiene carboxylic acid by either the intravenous or intraperitoneal or oral route to mice or rats produces a substantially decreased motor activity which appears one hour after administration of the compound.

The ability of the compounds of general Formula I to inhibit γ-aminobutyric acid transaminase may be determined by in vitro or in vivo measures of γ-aminobutyric acid transaminase activity. For example, γ-aminobutyric acid levels are markedly increased in the brains of mice and rats after treatment with compounds of general Formula I at doses between 5 to 100 mg/kg by parenteral and oral routes. This ability is further shown by the protective effect of the treatment on audiogenic seizures in mice of the DBA strain measured by the general method described by Simlet et al., Biochem. Pharmacol. 22, 1701 (1973) which is currently used as evidence of antiepileptic activity.

The ability of the compounds of the present invention at doses ranging from 20 to 100 mg/kg to alleviate reserpine ptosis may be shown by the classical test of B. Rubin et al., J. Pharmacol. 120, 125 (1957), which is currently used to determine antidepressant activity.

As indicated hereinabove the compounds of the present invention have been found to offer certain advantages over gabaculine which is a known inhibitor of γ-aminobutyric acid transaminase in that the compounds of the present invention are more effective inhibitors of the enzyme. Also, compounds of the present invention wherein $R_3$ is bromine are more lipophilic and hence should more readily penetrate the blood-brain barrier. The compounds of the present invention are particularly effective in decreasing γ-aminobutyric acid transaminase activity and elevating γ-aminobutyric acid levels in the brain.

The compounds of the present invention can be administered in various manners to the patient being treated to achieve the desired effect. The compounds can be administered alone or in the form of a pharmaceutical preparation orally, parenterally, for example, intravenously, intraperitoneally, subcutaneously or topically. The amount of compound administered will vary over a wide range and can be any effective amount. Depending on the patient to be treated, the condition being treated and the modes of administration, the effective amount of compound administered will vary from about 0.1 mg/kg to 150 mg/kg of body weight of the patient per unit dose and preferably will be about 10 mg/kg to about 100 mg/kg of body weight of patient per unit dose. For example, a typical unit dosage form may be a tablet containing from 10 to 200 mg of a compound of Formula I which may be administered to the patient being treated from 1 to 4 times daily to achieve the desired effect.

As used herein the term patient is taken to mean warm blooded animals, such as, mammals, for example, cats, dogs, rats, mice, guinea pig, horses, bovine cows and sheep.

The solid unit dosage forms can be of the conventional type. Thus, the solid form can be a capsule which can be of the ordinary gelatin type containing a novel compound of this invention and a carrier, for example, lubricants and inert fillers such as lactose, sucrose and corn starch. In another embodiment, the novel compounds are tableted with conventional tablet bases such as lactose, sucrose, or corn starch in combination with binders such as acacia, corn starch or gelatin, disintegrating agents such as corn starch, potato starch or alginic acid, and a lubricant such as stearic acid or magnesium stearate.

For parenteral administration the compounds may be administered as injectable dosages of a solution or suspension of the compound in a physiologically acceptable diluent with a pharmaceutical carrier which can be a sterile liquid such as water and oil with or without the addition of a surfactant and other pharmaceutically acceptable adjuvants. Illustrative of oils which can be employed in these preparations are those of petroleum, animal, vegetable or synthetic origin, for example, peanut oil, soybean oil and mineral oil. In general, water, saline, aqueous dextrose and related sugar solutions, ethanol and glycols such as propylene glycol or polyethylene glycol are preferred liquid carriers particularly for injectable solutions.

The compounds can then be administered in the form of a depot injection or implant preparation which may be formulated in such a manner as to permit a sustained release of the active ingredients therein. The active ingredient can be compressed into pellets or small cylinders and implanted subcutaneously or intramuscularly as depot injections or implants. Implants may employ inert materials such as biodegradable polymers or synthetic silicones.

Following are illustrative examples of pharmaceutical preparations containing the compounds of the present invention.

|  | Per tablet |
|---|---|
| a 3-amino-1,5-cyclohexadienecarboxylic acid | 20.0 mg |
| b wheat starch | 95.0 mg |
| c lactose | 33.5 mg |
| d magnesium stearate | 1.5 mg |

A portion of the wheat starch is used to make a granulated starch paste which together with the remainder of the wheat starch and the lactose is granulated, screened and mixed with the active ingredient (a) and the magnesium stearate. The mixture is compressed into tablets weighing 150 mg each.

An illustrative composition for a parenteral injection is the following, wherein the quantities are on a weight to volume basis:

|  | Amount |
|---|---|
| a 3-amino-1,5-cyclohexadienecarboxylic acid | 50.0 mg |
| b sodium chloride | q. s. |
| c water for injection to make | 20.0 ml |

The composition is prepared by dissolving the active ingredient (a) and sufficient sodium chloride in water for injection to render the solution isotonic. The composition may be dispensed in a single ampule containing 50 mg of the active ingredient for multiple dosage or in 20 ampules for single dosage.

An illustrative composition for hard gelatin capsules is as follows:

|  | Amount |
|---|---|
| a 3-amino-1,5-cyclohexadienecarboxylic acid | 100.0 mg |
| b talc | 35.0 mg |

The composition is prepared by passing the dry powders of (a) and (b) through a fine mesh screen and mixing them well. The powder is then filled into N° 0 hard gelatin capsules at a net fill of 135 mg per capsule.

The preparation of the compounds of general Formula I wherein $R_1$ is hydrogen and $R_2$ is hydroxy may be depicted schematically as follows:

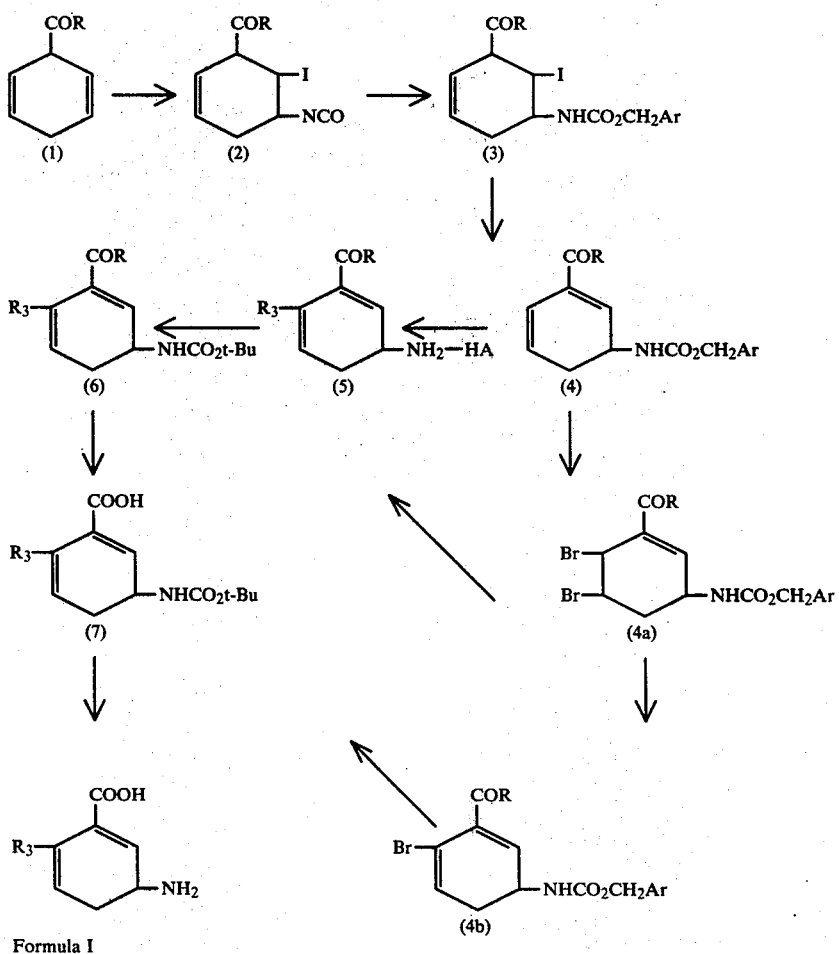

Formula I
$R_1 = H$, $R_2 = OH$

In the above schematic representation R is a straight or branched alkoxy group of from 1 to 6 carbon atoms, such as, methoxy, ethoxy, n-propoxy, isopropoxy, n-butoxy, tert-butoxy, n-pentoxy, neopentoxy or n-hexyloxy, benzyloxy, p-methoxybenzyloxy, 2,4-dimethoxybenzyloxy, trimethylsilyloxy; Ar is phenyl or p-methoxyphenyl; HA represents a mineral acid, such as hydrochloric, hydrobromic or trifluoroacetic acid; $R_3$ is hydrogen or bromine as defined in general Formula I; and t-Bu is tertiary-butyl.

The 2,5-cyclohexadiene carboxylic acid ester (1) is treated with silver cyanate in a solvent such as methlene chloride, chloroform, carbon tetrachloride, tetrahydrofuran or diethylether with the addition of solid iodine. The mixture is stirred for about 1 to 6 hours at about $-10°$ to $25°$ C. to give 2-iodo-3-isocyano-2-cyclohexene carboxylic acid ester (2) to which is added benzyl alcohol or p-methoxybenzyl alcohol with stirring for 6 to 18 hours optionally in the presence of a catalyst, such as diisobutyltin dilaurate or benzyloxylithium to give the carbamate (3) followed by treatment with one equivalent of a suitable hindered base, such as, diazabicyclooctane, diazabicyclononene, diazabicycloundecene or triethylamine in a solvent, such as, acetone, ether, tetrahydrofuran, methylenechloride, chloroform or dioxane at about $25°$ C. for about 1 to 4 hours to give the 3-carbamate-1,5-cyclohexadiene derivative (4). When $R_3$ in the compounds of general Formula I is bromine the dehydrodeiodinated derivative (4) is treated with 1 equivalent of bromine in a chlorinated hydrocarbon solvent, such as chloroform, methylene chloride or chlorobenzene or acetic acid at about $0°$ to $30°$ C. with stirring for about 8 to 24 hours to give the dibromo compound (4a). To the dibromo compound (4a) is added a strong base in an ether solvent, such as diethyl ether, tetrahydrofuran or dioxane or acetone after which the reaction mixture is stirred for about 15 to 30 hours at about $0°$ to $25°$ C. then quenched with water. The dehydrodeiodinated derivative, that is, compounds (4) or (4b) is treated with excess acid, for example, hydrochloric, hydrobromic or trifluoroacetic acid, the latter of which is preferred, in excess anisole or excess 1,3-dimethoxybenzene to give the acid addition salt (5). When R is other than trimethylsilyloxy, tert-butoxy, benzyloxy, 2,4-dimethoxybenzyloxy or p-methoxy-benzyloxy the acid addition salt or 3-amino-1,5-cyclohexaidene carboxylic acid ester or ether derivative (5) is reacted with 2-tert-butoxycarbonyloxyimino-2-phenylacetonitrile or tert-butylazidoformate in the presence of a base, such as, an alkylamine, for example, triethylamine, sodium hydroxide or potassium hydroxide in a solvent such as ethers, for example, diethyl ether or tetrahydrofuran, dimethyl formamide, chlorinated hydrocarbons, such as methylenechloride or chloroform at about $25°$ C. for about 1 to 24 hours followed by alkaline hydrolysis then acid hydrolysis and when the free base is desired treating with base by procedures well known in the art. Alkaline hydrolysis may be achieved, for example, by treatment with sodium hydroxide or potassium hydroxide for about 1 to 3 hours at about $25°$ C. to give the carbamate acid (7). Acid hydrolysis of the carbamate acid (7) may be achieved by, for example, treatment with hydrochloric, hydrobromic acid or trifluoroacetic acid in a lower alcohol solvent for about 1 to 20 hours at temperatures up to reflux. When in the carbamate ester derivative (4) R is trimethylsilyloxy, tert-butoxy, benzyloxy, 2,4-dimethoxybenzyloxy or p-methoxybenzyloxy said derivative, after treatment with trifluoroacetic acid and anisole, may be applied directly to an acid ion exchange resin to give the 3-amino-1,5-cyclohexadiene carboxylic acid derivative of Formula I.

Suitable strong bases which may be employed in the preparation of compounds of general Formula I wherein $R_3$ is bromine as described hereinabove are, hindered amines for example, diazabicyclooctane, diazabicyclononene or triethylamine.

The 2,5-cyclohexadiene carboxylic acid esters that is, compounds 1, used hereinabove may be obtained by various routes. For example, 2,5-cyclohexadiene carboxylic acid, which is known in the art, may be transformed to an ester derivative, that is, compound 1 wherein R is a straight or branched alkoxy group of from 1 to 6 carbon atoms, benzyloxy, 2,4-dimethoxybenzyloxy or p-methoxybenzyloxy by reaction with the appropriate alcohol in the presence of dicyclohexylcarbodiimide, thionyl chloride, trifluoroacetic anhydride or acid catalysts by procedures generally known in the art. Alternatively compound 1 wherein R is tert-butoxy may be prepared by treating 2,5-cyclohexadiene carboxylic acid in a chlorinated hydrocarbon solvent, such as, methylene chloride containing sulfuric acid with isobutylene. Compound 1 wherein R is trimethylsilyloxy may be prepared by treating 2,5-cyclohexadiene carboxylic acid with trimethylsilyl chloride in the presence of triethylamine. Also, compound 1 wherein R is trimethylsilyloxy may be prepared by treating 2,5-cyclohexadiene carboxylic acid methyl ester with trimethylsilyl iodide in a chlorinated hydrocarbon, such as, carbon tetrachloride, chloroform or methylene chloride at $50°$ C. for about 4 to 24 hours as generally described by M. E. Jung and M. A. Lyster, J. Am. Chem. Soc. 99, 968 (1977).

The compounds of general Formula I wherein $R_2$ is a straight or branched alkoxy group of from 1 to 8 carbon atoms are prepared from the corresponding derivatives wherein $R_2$ is hydroxy by reaction with an alcohol of the formula $R_8OH$ wherein $R_8$ is a straight or branched alkyl group of from 1 to 8 carbon atoms, such as, methyl, ethyl, n-propyl, isopropyl, n-butyl, tert-butyl, n-pentyl, neopentyl, or n-hexyl, saturated with HCl gas at about $25°$ C. for about 12 to 36 hours, or in the presence of p-toluenesulfonic acid.

The compounds of general Formula I wherein $R_2$ is $NR_5R_6$ wherein each of $R_5$ and $R_6$ is hydrogen or a lower alkyl group of from 1 to 4 carbon atoms are prepared by treating a functional derivative of the corresponding compound wherein $R_2$ is hydroxy, for example, an acid halide, such as, the acid chloride or an acid anhydride, and $R_1$ has the meaning defined in Formula I with an excess of an amine of the formula $HNR_5R_6$ wherein $R_5$ and $R_6$ have the meanings defined above with the proviso that any free amino group is suitably protected. The reaction is carried out in a solvent such as, methylene chloride, chloroform, dimethylformamide or ethers, such as, tetrahydrofuran and dioxane or benzene at about $25°$ C. for about 1 to 4 hours. Suitable amines are ammonia, or a compound which is a potential source of ammonia, such as hexamethylenetetramine; primary amines, for example, methylamine, ethylamine or m-propylamine; and secondary amines, for example, dimethylamine, diethylamine, or di-n-butylamine. Following the reaction the amine protecting groups are removed by treatment with acid, for example, trifluoroacetic acid or hydrogen bromide in dioxane.

The compounds of general Formula I wherein $R_2$ is

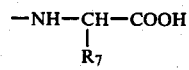

wherein $R_7$ is hydrogen, a straight or branched lower alkyl group of from 1 to 4 carbon atoms, benzyl or p-hydroxybenzyl are prepared by reacting an acid anhydride, of the corresponding derivative wherein $R_2$ is hydroxy, and $R_1$ has the meaning defined in Formula I with the proviso that any free amino group is protected with a suitable blocking group such as benzyloxycarbonyl or tert-butoxycarbonyl with a compound of the formula

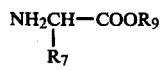

wherein $R_7$ has the meaning defined hereinabove, and $R_9$ is a lower alkyl group, such as, methyl or ethyl in an ether solvent, such as, tetrahydrofuran or dioxane in the presence of a base, such as, triethylamine at about 0° to 50° C. for about 1 to 24 hours followed by acid hydrolysis, for example, with trifluoroacetic acid or hydrogen bromide in dioxane and base hydrolysis using, for example, sodium hydroxide or sodium borate at a temperature of about 0° to 25° C. for about ½ hour to 6 hours.

The compounds of general Formula I wherein $R_1$ is alkylcarbonyl wherein the alkyl moiety has from 1 to 4 carbon atoms and is straight or branched and $R_2$ is hydroxy or an alkoxy group of from 1 to 8 carbon atoms are prepared by treating the corresponding derivative wherein $R_1$ is hydrogen with an acid halide of the formula

halo wherein halo is a halogen atom, such as, chlorine or bromine and $R_{10}$ is a straight or branched alkyl group having from 1 to 4 carbon atoms, such as, methyl, ethyl, n-propyl, isopropyl, n-butyl and tert-butyl, or an appropriate acid anhydride, in water in the presence of a base, such as, sodium hydroxide or sodium borate such as dichloromethane or in a chlorinated solvent amine base such as in the presence of an triethylamine at a temperature of about 0° to 25° C. for about ½ hour to 24 hours.

The compounds of general Formula I wherein $R_1$ is alkoxycarbonyl wherein the alkoxy moiety is straight or branched and has from 1 to 4 carbon atoms are prepared by treating the corresponding derivative wherein $R_2$ is a lower alkoxy group, such as, methoxy or ethoxy and $R_1$ is hydrogen with an alkyl haloformate of the formula halo-

wherein $R_{11}$ is a straight or branched alkyl group of from 1 to 4 carbon atoms, such as, methyl, ethyl, n-propyl, isopropyl, n-butyl or tert-butyl, and halo is halogen, such as, chlorine or bromine, in water in the presence of a base, such as, sodium hydroxide or sodium borate or in dichloromethane in the presence of triethyl amine at a temperature of about 0° to 25° C. for about ½ hour to 6 hours followed by base hydrolysis, using for example, sodium hydroxide or sodium borate at a temperature of about 0° to 25° C. for about ½ hour to 6 hours.

The compounds of general Formula I wherein $R_1$ is

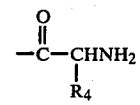

wherein $R_4$ is hydrogen, a straight or branched alkyl group having from 1 to 4 carbon atoms, benzyl or p-hydroxybenzyl are prepared by treating the corresponding derivative wherein $R_2$ is a lower alkoxy group, such as, methoxy or ethoxy and $R_1$ is hydrogen with an acid of the formula

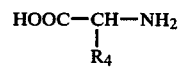

or an anhydride thereof wherein the amino group is protected with a suitable blocking group, such as, benzyloxycarbonyl or tert-butoxycarbonyl and $R_4$ has the meaning defined above in an ether, such as, tetrahydrofuran or dioxane, or a chlorinated hydrocarbon, such as, methylene chloride or chloroform, and in the presence of a dehydrating agent, such as, dicyclohexylcarbodiimide when the free acid is employed, at a temperature of about 0° to 35° C. for about 1 to 12 hours followed by base hydrolysis, using for example, sodium hydroxide or sodium borate and acid hydrolysis using, for example, trifluoroacetic acid or HBr/dioxane at a temperature of about 0° to 25° C. for about ½ hour to 6 hours.

The following examples further illustrate the invention.

EXAMPLE 1

Methyl 3-(p-methoxybenzyloxycarbonylamino)-1,5-cyclohexadiene

To 10 g of potassium cyanate in 140 ml of water is added 20 g of silver nitrate in 600 ml of water. The white precipitate is filtered off and washed with water, methanol and anhydrous ether. The solid is dryed in vacuo for 2 hours to afford 17.7 g of silver cyanate which is suspended in 150 ml methlene chloride and cooled in an ice-salt bath. To the suspension is added 15.1 g (109 m mole) of methyl 2,5-cyclohexadienecarboxylate followed by 27.70 (109 m mole) of solid iodine in small portions during 20 minutes. The mixture is maintained in cooling baths for 1 hour then stirred at about 25° C. for 4 hours. The mixture is filtered through celite and concentrated after which 15.1 g (109 m mole) of p-methoxybenzyl alcohol is added. The mixture is stirred over night at about 25° C., and then 200 ml of acetone is added followed by 12.2 g (109 m mole) of diazabicyclooctane. After 2 hours at 25° C. the solution is evaporated and the residue is taken up in ether and water. The organic base is dryed and evaporated. The residue is recrystallized from chloroform-petrol to afford 16.5 g of methyl 3-(p-methoxybenzyloxycarbonylamino)-1,5-cyclohexadienecarboxylate.

EXAMPLE 2

Methyl 3-(tert-butoxycarbonylamino)-1,5-cyclohexadienecarboxylate

To a suspension of 16.5 g of methyl 3-(p-methoxybenzyloxycarbonylamino)-1,5-cyclohexadienecarboxylate in 40 ml of anisole at about 25° C. is added slowly 30 ml of trifluoroacetic acid. After the addition of the first 5 ml the solid dissolves. The solution is cooled in a ice bath and the addition of trifluoroacetic acid continues. The solution is maintained at 0° C. for one hour, then the solvents are removed in vacuo (1 mm) maintaining the temperature below 40° C. The resulting oily residue is cooled to 0° C. and anhydrous ether added with stirring. The precipitate is filtered off to give 8.1 g of methyl 3-amino-1,5-cyclohexadienecarboxylate trifluoroacetate.

A solution of 7.4 g (27.7 m mole) of the above obtained trifluoroacetate in 50 ml of tetrahydrofuran treated with 17.8 g (31.8 m mole) of tert-butoxycarbonyloxyimino-2-phenylacetonenitrile and 10 ml of triethylamine. The solution is stirred over night at about 25° C. then diluted with ether, washed with water, dryed and evaporated to give methyl 3-(tert-butoxycarbonylamino)-1,5-cyclohexadienecarboxylate.

EXAMPLE 3

3-Amino-1,5-cyclohexadiene carboxylic acid 1.4 g of methyl 3-(tert-butoxycarbonylamino)-1,5-cyclohexadienecarboxylate is treated with 164 mg of sodium hydroxide in 2 ml of methanol and 1 ml of water. The solution is stirred at about 25° C. for 3 hours, acidified to a pH of 3 with dilute hydrochloric acid and evaporated to dryness in vacuo. The residue is treated with 7 ml of methanol and 3.5 ml of 5% hydrochloric acid for 24 hours at 25° C. after which the solution is concentrated and washed with ether. The aqueous phase is evaporated in vacuo, and the residue is recrystallized from methanol-ether to afford 20 mg of 3-amino-1,5-cyclohexadiene carboxylic acid hydrochloride. M.P. 180°-184° C.

EXAMPLE 4

Ethyl 3-Amino-1,5-cyclohexadienecarboxylate hydrochloride

3-Amino-1,5-cyclohexadiene carboxylic acid hydrochloride (200 mg) is dissolved in ethanol containing anhydrous HCl, and the resulting solution is stirred over night at 0° C. Evaporation of the solvent affords ethyl 3-amino-1,5-cyclohexadienecarboxylate hydrochloride.

EXAMPLE 5

N-propyl-3-amino-1,5-cyclohexadienecarboxamide hydrochloride

A solution of 240 mg (1 m mole) of 3-tert-butoxycarbonylamino-1,5-cyclohexadiene carboxylic acid in 5 ml of dichloromethane is treated with 202 mg (2 m mole) of triethylamine and 94 mg (1 m mole) of methyl chloroformate. After 30 minutes at 25° C. the solution is treated with 60 mg (1 m mole) of n-propylamine for 1 hour at 25° C. after which the solution is diluted with dichloromethane, washed with water, dryed and evaporated. The residue is stirred for 18 hours in 7 ml of methanol and 3.5 ml of 5% aqueous HCl. Evaporation affords N-propyl-3-amino-1,5-cyclohexadienecarboxamide hydrochloride.

EXAMPLE 6

N-(3-amino-1,5-cyclohexadienyl)carbonylalanine hydrochloride

A solution of 240 mg (1 m mole) of 3-tert-butoxycarbonylamino-1,5-cyclohexadiene carboxylic acid and 5 ml of dichloromethane is treated with 202 mg (2 m mole) of triethylamine and 94 mg (1 mole) of methyl chloroformate. After 30 minutes at 25° C. the solution is treated with 103 mg (1 m mole) of alanine methylester and maintained at 25° C. for 1 hour after which the solution is washed with water, dryed and concentrated. The residue is treated with 3 ml of methanol and 120 mg of sodium hydroxide in 2 ml of water for 3 hours at 25° C. then solidified and extracted with dichloromethane. The organic phase is dryed and concentrated. The residue is treated with 7 ml of methanol containing 5% HCl for 18 hours at 25° C. Evaporation affords N-(3-amino-1,5-cyclohexadienyl)carbonylalanine hydrochloride.

EXAMPLE 7

3-Acetamido-1,5-cyclohexadiene carboxylic acid.

A solution of 190 mg (1 m mole) of methyl 3-amino-1,5-cyclohexadienecarboxylate hydrochloride in 5 ml of dichloromethane is treated with 78 mg (1 m mole) of acetyl chloride and 202 mg (2 m mole) of triethylamine for 1 hour at 25° C. after which the solution is washed with water, dryed and concentrated. The residue is treated at 25° C. with 3 ml of methanol and 100 ml of sodium hydroxide in 200 ml of water for 3 hours then acidified and extracted with dichloromethane. The organic phase is dried and evaporated to afford 3-acetamido-1,5-cyclohexadiene carboxylic acid.

EXAMPLE 8

3-Alanylamino-1,5-cyclohexadiene carboxylic acid hydrochloride

A solution of 188 mg (1 m mole) of tert-butoxycarbonylalanine in 5 ml of dichloromethane is treated with 101 mg (1 m mole) of triethylamine and 94 mg (1 m mole) of methyl chloroformate then added to a solution of 190 mg (1 m mole) of methyl 3-amino-1,5-cyclohexadienecarboxylate hydrochloride and 101 mg (1 m mole) of triethylamine in 5 ml of dichloromethane. After 1 hour at 25° C. the solution is washed with water, dried and evaporated. The residue is treated for 3 hours at 25° C. with 3 ml of methanol, 100 mg of sodium hydroxide and 2 ml of water then acidifie and extracted with dichloromethane. The organic phase is dryed and concentrated. The residue is treated with 7 ml of methanol containing 3.5 ml of 5% HCl for 18 hours at 25° C. then concentrated to afford 3-alanylamino-1,5-cyclohexadiene carboxylic acid hydrochloride.

EXAMPLE 9

Methyl 3-tert-butoxycarbonylamino-6-bromo-1,5-cyclohexadienecarboxylate

A solution of 2.53 g (10 m mole) of methyl 3-(tert-butoxycarbonylamino)-1,5-cyclohexadienecarboxylate in 40 ml of carbontetrachloride at 0° C. is treated dropwise with 1.60 g (10 m mole) of bromine. The solution is stirred at 25° C. for 12 hours, then evaporated under reduced pressure to afford the crude dibromide which is dissolved in 40 ml of acetone and treated with 1.2 g (10 m mole) of diazabicyclooctane for 12 hours at 25° C. The solvent is evaporated under reduced pressure, and the residue is treated with ether and water. The organic phase is dried and evaporated to afford methyl 3-tert-butoxycarbonylamino-6-bromo-1,5-cyclohexadienecarboxylate.

EXAMPLE 10

3-Amino-6-bromo-1,5-cyclohexadiene carboxylic acid

A solution of 600 mg of methyl 3-tert-butoxycarbonylamino-6-bromo-1,5-cyclohexadienecarboxylate in 2 ml of methanol is treated with 150 mg of sodium hydroxide in 2 ml of water at 25° C. for 2 hours. Acidification of the mixture with 0.5 N HCl gives a precipitate which is collected to afford 6-bromo-3-tert-butoxycarbonylamino-1,5-cyclohexadiene carboxylic acid. A solution of 250 mg of the thus obtained carboxylic acid in 4 ml of methanol is treated with 2 ml of 5% aqueous HCl at 25° C. for 20 hours. The solution is concentrated to half volumn under reduced pressure and treated with acetone. The resulting precipitate is collected to afford 3-amino-6-bromo-1,5-cyclohexadiene carboxylic acid hydrochloride.

EXAMPLE 11

N-Propyl-3-acetamido-1,5-cyclohexadienecarboxamide

A solution of 180 mg (1 m mole) of 3-acetamido-1,5-cyclohexadiene carboxylic acid in 5 ml of dichloromethane is treated with 202 mg (2 m mole) of triethylamine and 94 mg (1 m mole) of methylchloroformate. After 30 minutes at 25° C. the solution is treated with 60 mg (1 m mole) of n-propylamine for 1 hour at 25° C. after which the solution is diluted with dichloromethane and, washed with water, dried and evaporated to give N-propyl-3-acetamido-1,5-cyclohexadienecarboxamide.

EXAMPLE 12

N-Propyl-3-(2-aminopropionamido)-1,5-cyclohexadienecarboxamide trifluoroacetate

A solution of 310 mg (1 m mole) of 3-(2-tert-butoxycarbonylaminopropionylamido)-1,5-cyclohexahexadiene carboxylic acid in 5 ml of dichloromethane is treated with 202 mg (2 m mole) of triethylamine and 94 mg (1 m mole) of methyl chloroformate. After 30 minutes at 25° C. the solution is treated with 60 mg (1 m mole) of n-propylamine for 1 hour at 25° C. after which the solution is diluted with dichloromethane and washed with water. The organic phase is dried and concentrated leaving a residue which is treated with 2 ml of trifluoroacetic acid for 1 hour at 25° C. then diluted with anhydrous ether. The precipitated trifluoroacetate salt is filtered off to afford N-propyl-3-(2-aminopropionamido)-1,5-cyclohexadienecarboxamide trifluoroacetate.

EXAMPLE 13

N-(2-Propionic acid)-3-acetamido-1,5-cyclohexadienecarboxamide

A solution of 180 mg (1 m mole) of 3-acetamido-1,5-cyclohexadiene carboxylic acid in 5 ml of dichloromethane is treated with 202 mg (2 m mole) of triethylamine and 94 mg (1 m mole) of methyl chloroformate. After 35 minutes at 25° C. the solution is treated with 103 mg (1 m mole) of alanine methylester and maintained at 25° C. for 1 hour after which the solution is washed with water, dried and concentrated. The resulting residue is treated with 3 ml of methanol and 120 mg of sodium hydroxide in 2 ml of water for 3 hours at 25° C., then acidified and extracted with dichloromethane. The organic phase is dried and concentrated to afford N-(2-propionic acid)-3-acetamido-1,5-cyclohexadienecarboxamide.

EXAMPLE 14

N-(2-Propionic acid)-3-(2-aminopropionamido)-1,5-cyclohexadienecarboxamide trifluoroacetate A solution of 310 mg (1 m mole) of 3-(2-tert-butoxycarbonylaminopropionylamido)-1,5-cyclohexadiene carboxylic acid in 5 ml of dichloromethane is treated with 202 mg (2 m mole) of triethylamine and 94 mg (1 m mole) of methyl chloroformate. After 30 minutes at 25° C. the solution is treated with 103 mg (1 m mole) of alanine methylester and maintained at 25° C. for 1 hour after which the solution is washed with water, dried and concentrated. The resulting residue is treated with 3 ml of methanol and 120 mg of sodium hydroxide in 2 ml of water for 3 hours at 25° C. then acidified and extracted with dichloromethane. The organic phase is dried and concentrated leaving a residue which is treated with 2 ml of trifluoroacetic acid for 1 hour at 25° C. then diluted with anhydrous ether. The precipitated trifluoacetate salt is filtered off to afford N-(2-propionic acid)-3-(2-aminopropionamido)-1,5-cyclohexadienecarboxamide trifluoroacetate.

EXAMPLE 15

3-Amino-1,5-cyclohexadiene carboxylic acid trifluoroacetate

A solution of 16 g of 2,5-cyclohexadiene carboxylic acid in 20 ml of dichloromethane containing 10 drops of sulfuric acid is treated with 40 ml of isobutylene in an autoclave overnight after which the contents were poured into a sodium bicarbonate solution. The organic phase is isolated and passed through alumina to afford tert-butyl 2,5-cyclohexadienecarboxylate.

To 5.4 g (30 m mole) of tert-butyl 2,5-cyclohexadienecarboxylate and 4.9 g (33 m mole) of silver cyanate in 50 ml of dichloromethane is added 7.6 g (30 m mole) of iodine at 0° C. After 1 hour at 0° C. and 3 hours at 25° C. the mixture is filtered and the filtrate concentrated leaving a residue to which is added 3.8 g (30 m mole) of p-methoxybenzyl alcohol. The mixture is stirred overnight at 25° C. after which 50 ml of acetone is added followed by 3.3 g (30 m mole) of diazabicyclooctane. After 2 hours at 25° C. the solvent is evaporated, and the residue partitioned between ether and 1 N HCl. The ether solution is dried and concentrated leaving a residue which is chromatographed on silica. The fraction containing the benzylcarbamate is treated with 6 ml of anisole and 6 ml of trifluoroacetic acid for 1 hour at 0° C. The solvents are removed in vacuo and the residue triturated with ether. The resulting solid is collected and treated with 2 ml of trifluoroacetic acid for 1 hour at 25° C. after which ether is added and the precipitate collected. The precipitate is recrystallized from isopropanol-ether to afford 3-amino-1,5-cyclohexadiene carboxylic acid trifluoroacetate. M. P. 166° C. The individual optical isomers of general formula I are included within the scope of the invention. These may be prepared from the racemate by using (+) or (−) binaphthyl phosphoric acid as described by R. Viterbo et al., Tetrahedron Letters 48, 4617–4620 (1971) and in U.S. Pat. No. 3,848,030. Other resolving agents such as (+) camphor-10-sulfonic acid may also be employed.

We claim:

1. A compound of the formula

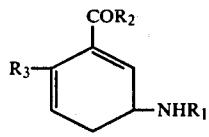

wherein $R_1$ is hydrogen; $R_2$ is hydroxy, or a straight or branched alkoxy group of from 1 to 8 carbon atoms; $R_3$ is hydrogen or bromine; and pharmaceutically acceptable salts and individual optical isomers thereof.

2. A compound of claim 1 wherein $R_3$ is hydrogen.
3. A compound of claim 1 wherein $R_3$ is bromine.
4. A compound of claim 1 wherein $R_2$ is hydroxy.
5. A compound of claim 4 which is 3-amino-1,5-cyclohexadiene carboxylic acid or a pharmaceutically acceptable salt thereof.
6. The compound of claim 4 which 3-amino-1,5-cyclohexadiene carboxylic acid trifluoroacetate.
7. A compound of claim 6 which is 3-amino-6-bromo-1,5-cyclohexadiene carboxylic acid or a phramceutically acceptable salt thereof.
8. A pharmaceutical composition in unit dosage form which comprises an effective amount of a compound of claim 1 and a significant quantity of a pharmaceutically acceptable carrier.
9. A composition of claim 8 wherein the effective quantity of compound is from 0.1 mg/kg to 150 mg/kg of body weight of the patient per unit dose.